United States Patent
Shuman (10) Patent No.: US 11,234,790 B2
(45) Date of Patent: Feb. 1, 2022

(54) DEVICES AND METHODS FOR DELIVERING A FIDUCIAL MARKER

(71) Applicant: GYRUS ACMI, INC., Southborough, MA (US)

(72) Inventor: Brandon J. Shuman, Kirkland, WA (US)

(73) Assignee: GYRUS ACMI, INC., Southborough, MA (US)

( * ) Notice: Subject to any disclaimer, the term of this patent is extended or adjusted under 35 U.S.C. 154(b) by 320 days.

(21) Appl. No.: 16/085,645

(22) PCT Filed: Mar. 22, 2016

(86) PCT No.: PCT/US2016/023614
§ 371 (c)(1),
(2) Date: Sep. 17, 2018

(87) PCT Pub. No.: WO2017/164851
PCT Pub. Date: Sep. 28, 2017

(65) Prior Publication Data
US 2019/0105124 A1 Apr. 11, 2019

(51) Int. Cl.
*A61B 90/00* (2016.01)
*A61B 17/00* (2006.01)

(52) U.S. Cl.
CPC ........ *A61B 90/39* (2016.02); *A61B 17/00234* (2013.01); *A61B 2017/0053* (2013.01); *A61B 2017/00867* (2013.01); *A61B 2090/3908* (2016.02); *A61B 2090/3987* (2016.02); *A61B 2090/3991* (2016.02)

(58) Field of Classification Search
CPC .............. A61B 90/39; A61B 17/00234; A61B 2017/0053; A61B 2017/00867; A61B 2090/3908; A61B 2090/3987; A61B 2090/3991
See application file for complete search history.

(56) References Cited

U.S. PATENT DOCUMENTS

| | | | | |
|---|---|---|---|---|
| 5,271,414 A | * | 12/1993 | Partika | A61B 10/0266 600/567 |
| 5,853,366 A | * | 12/1998 | Dowlatshahi | A61B 90/39 600/434 |
| 7,001,341 B2 | * | 2/2006 | Gellman | A61B 10/0275 600/562 |
| 8,855,747 B2 | * | 10/2014 | Murray | A61N 5/1001 600/433 |

(Continued)

*Primary Examiner* — Christopher Koharski
*Assistant Examiner* — Kaitlyn E Selmer
(74) *Attorney, Agent, or Firm* — Clements Bernard Baratta; Michael S. Smith (57) ABSTRACT

A device for providing a fiducial marker(s) within or near a target tissue (e.g. nodule, tumor or other) within a patient. The present teachings provide a device with a handle device, a catheter with a distal end and a proximal end coupled to the handle device, a needle slidably received within the catheter, and a stylet slidably received within the needle. The stylet includes a fiducial marker at a distal end of the stylet. The fiducial marker transitions from a first shape state to a second shape state upon expulsion from the distal end of the needle. The distal end of the stylet is mechanically disconnected from the proximal end of the fiducial marker during a fiducial marker delivery state.

11 Claims, 8 Drawing Sheets

(56) References Cited

U.S. PATENT DOCUMENTS

| | | | |
|---|---|---|---|
| 10,342,635 B2* | 7/2019 | Field | A61B 90/39 |
| 2001/0023322 A1* | 9/2001 | Espositio | A61B 17/320068 |
| | | | 600/564 |
| 2003/0195433 A1* | 10/2003 | Turovskiy | A61B 90/39 |
| | | | 600/564 |
| 2008/0319341 A1* | 12/2008 | Taylor | A61B 10/0275 |
| | | | 600/567 |

* cited by examiner

DEVICES AND METHODS FOR DELIVERING A FIDUCIAL MARKER

FIELD

The present teachings relate to medical devices, and more particularly, to improved methods and devices for delivering fiducial markers at a target tissue.

BACKGROUND

Various imaging modalities are used to investigate, diagnose and treat people who may be suffering from various conditions and injuries. Photographs, X-ray, Magnetic Resonance Imaging (MRI), Ultrasound, and other imaging modalities have various advantages, disadvantages, and application specific features. Generally, with respect to a given imaging modality it is desirable for a review of any resultant images to have a reference point relative to the subject depicted in an image. Various types of coordinate schemes and markers are used to facilitate identifying positions of interest in a given image.

SUMMARY

The present teachings provides a fiducial marker(s) within or near a target tissue (e.g. nodule, tumor or other) within a patient. The present teachings provide a device with a handle device, a catheter with a distal end and a proximal end coupled to the handle device, a needle slidably received within the catheter, a stylet slidably received within the needle and a fiducial marker received within the needle. The needle includes a distal end and a proximal end coupled to the handle device. The stylet includes a distal end and a proximal end coupled to the handle device. The fiducial marker includes a proximal end and a distal end. The fiducial marker is in a first shape state inside the needle. The fiducial marker transitions from the first shape state to a second shape state upon expulsion from the distal end of the needle. The distal end of the stylet is in mechanical communication with the proximal end of the fiducial marker when the proximal end of the fiducial marker remains within the needle. The distal end of the stylet is mechanically disconnected from the proximal end of the fiducial marker during a fiducial marker delivery state.

In one teaching, the stylet is mechanically disconnected from the fiducial marker as a result of a proximal retraction of the stylet after the fiducial marker has been positioned external to the needle.

In another teaching, the device includes a cartridge device having a housing with a proximal end and a distal end and a plunger. The distal end of the housing attaches to the handle device. The housing receives the fiducial marker when in the first shape state. When activated by a user, the plunger moves the fiducial marker to the distal end of the housing and into the handle device.

In still another teaching, the stylet and the fiducial marker are opposing ends of a monolithic material. The monolithic material includes a failure section located near the proximal end of the fiducial marker and the distal end of the stylet. The failure section includes a notch. Separation of the stylet from the fiducial marker occurs after application of a force to the notch during the fiducial marker delivery state. The second shape state comprises a shape set coil shape. The notch is located adjacent to an external circumference edge of the shape set coil shape.

In yet another teaching, the device further includes a fuse-like section located between the stylet and the fiducial marker. Separation of the stylet from the fiducial marker (i.e., failure of the fuse-like section) occurs after application of a current to the stylet and the fiducial marker with assistance from a grounding pad during the fiducial marker delivery state. The fuse-like section includes a cross section having a smaller area than cross sections of the distal end of the stylet and the proximal end of the fiducial marker.

In still yet another teaching, the second shape state comprises a shape set coil shape that produces preliminary failure at the failure section. Separation of the stylet from the fiducial marker occurs after application of a force to the fiducial marker during the fiducial marker delivery state.

DETAILED DESCRIPTION

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the description herein, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

While the teachings herein refer to and reference terms like "bronchoscope", "lymph node", "nodule", "device", "needle", "sampling needle", "fiducial markers" and the like, it is understood that these terms are broad, and the teachings herein can be used without limitation. In other words, the teachings herein may be suitable for illuminating other vessels, passages, lumens, body cavities, anatomy, tissue, organs, the like, or a combination thereof in humans and animals. One or more devices may function to deposit fiducial marker(s) ("fiducial(s)") within a target tissue, thus improving visibility of the target tissue via ultrasound or some other imaging device. The one or more devices may include one or more bronchoscopes.

The one or more bronchoscopes may be or may provide a device for attaching to a fiducial delivery device that can deposit one or more fiducials into a target tissue. The one or more bronchoscopes may provide for insertion, manipulation, and operation of various surgical instruments in the anatomy of a patient. The one or more bronchoscopes may provide for delivery of one or more fiducials into the anatomy. The one or more bronchoscopes may be used to visually inspect a site of interest, like the airways and lungs of a patient. The one or more bronchoscopes may be used to examine, treat, and/or diagnose lung growth, lung problems, lung cancer, lymph node(s), atelectasis, suspected interstitial lung disease, a lung rejection after a lung transplant, and/or to remove fluid or mucus plugs from the airways of a patient. The one or more bronchoscopes may be at least partially flexible, at least partially rigid, or both. The one or more bronchoscopes may include one or more ultrasound probes.

One or more catheters may function to provide a channel, a lumen, an opening, and/or a passageway for one or more devices to be advanced and/or introduced into the anatomy. The one or more catheters may function to introduce into the anatomy one or more medical devices, needles, transbronchial needle aspiration devices, cytology brushes, biopsy forceps, guiding devices, ultrasonic probes, illumination devices, therapies (i.e., chemotherapy, proteinomics, microspheres, etc.), fiducials, the like, or a combination thereof. The one or more catheters may be used to remove or expel from the anatomy one or more devices, fluids, tissue samples, abnormalities, foreign matter, or a combination thereof. The one or more catheters may each contain one or more lumen. The one or more catheters may include one or more sections that are generally rigid, one or more sections that are generally flexible, or a combination of both. The one or more catheters may include one or more sections that are generally rigid, generally flexible, or a combination of both. The one or more catheters may be at least partially flexible, bendable, articulable, or a combination thereof so that access to regions of interest can be easily obtained. The one or more catheters may bend or articulate 15 degrees or more, 45 degrees or more, 60 degrees or more, 90 degrees or more, 110 degrees or more, or even 130 degrees or more. The one or more catheters may be fabricated from a polymer, nylon, silicon, or any other suitable material. An outer surface of the one or more catheters may include a lubricant to facilitate insertion into, and removal from, the anatomy, the bronchoscope, a working channel of the bronchoscope, or a combination thereof. The one or more catheters may be elongated tubular members. The one or more catheters may extend along a longitudinal axis, a catheter axis, or both. The one or more catheters may include a uniform cross section, or the cross section may vary, taper, widen, narrow, or a combination thereof. The cross section of the one or more catheters may be circular, oval, irregular, and/or any other suitable shape or configuration. The cross section of the one or more catheters may be expandable, collapsible, formable, deformable, or a combination thereof. The one or more catheters may be configured to house, contain and/or protect any size or gauge needle. For example, the one or more catheters may house, contain, and/or protect about a 25 gauge needle or more, about a 22 gauge needle, about a 21 gauge needle, about a 19 gauge needle or less, etc. An outer surface of the one or more catheters may include one or more echogenic features or scribes. The one or more catheters may include one or more echogenic features so that the position and orientation of the catheter, the device, the needle, the needle tip, or a combination thereof can be viewed. The one or more catheters may include or define a hole or opening at a distal end, a proximal end, at a region in between, or a combination thereof so that one or more devices or instruments can pass therethrough. The one or more catheters may include or define an inner surface, an inner diameter, an inner portion, or a combination thereof that is dimensioned to generally conform to the outer diameter of the one or more needles or the one or more fiducials.

The one or more needles may function to be advanced into the anatomy to penetrate a site or region of interest. The one or more needles may function to puncture a region of interest so that the one or more fiducials can be deposited. The one or more needles may also function to provide medicine, therapy, or both to the anatomy. The one or more needles may also function to provide, develop, or have a local vacuum to a distal end or at a distal tip thereof. The one or more needles may be advanced towards and retracted from the region of interest via one or more catheters, devices, bronchoscopes, a needle handle, or a combination thereof. The one or more needles may be at least partially contained within the catheter. The one or more needles may be moved, advanced, retracted, or a combination thereof in the catheter. The one or more needles may have a length that extends along a longitudinal axis, a needle axis, or both. The one or more needles may have a constant cross section, a varying cross section, a tapered cross section, an irregular cross section, or a combination thereof. The cross section of the one or more needles may be generally circular, oval, irregular, or any other suitable shape. The one or more needles may be generally hollow. The one or more needles may include a generally concentric outer diameter and inner diameter. The one or more needles may have an outer diameter and an inner diameter, one or more of which may have a constant size along a length of the needle. The one or more needles may have an outer diameter and an inner diameter, one or more of which may vary, taper, slope, change, or a combination thereof. The one or more needles may be formed from a single material, or may be formed from one or more materials. The one or more needles may be fabricated from any material suitable for use in medical procedures. The one or more needles may be made from a metal or metal alloy, such as stainless steel, nitinol, or the like. The one or more needles may comprise a polymer or other suitable covering. The one or more needles may be generally rigid, generally flexible, or both. The one or more needles may include one or more portions or sections that are generally rigid, one or more portions or sections that are generally flexible, or both. The one or more needles may be at least partially flexible, bendable, articulable, or a combination thereof so that access to regions of interest can be easily obtained. The one or more needles may bend or articulate about 15 degrees or more, about 45 degrees or more, about 60 degrees or more, about 0 degrees or more, about 110 degrees or more, or even about 130 degrees or more. The one or more needles may be constructed from one or more hypotubes. The one or more needles may be constructed from one or more hypotubes that are relatively smooth and able to freely slide, rotate, or otherwise move within a catheter, a bronchoscope, a device, the anatomy, or a combination thereof. The one or more needles may include one or more holes, ports, slots, apertures, openings, the like, or a combination thereof at the distal end, a proximal end, or a location therebetween. The one or more needles may include one or more holes, ports, slots, the like or a combination thereof for tissue sample collection; for introducing one or more fiducial devices or stylet into the needle; for introducing one or more fiducial devices into the anatomy; for introducing medicine or therapy to the anatomy; or a combination thereof.

The one or more needles may be any size or gauge. That is, the one or more needles may be about 25 gauge or more, about 22 gauge, about 21 gauge, or about 19 gauge or less, etc. The one or more needles may include a combination of two or more gauges. That is, for example, a proximal portion of the needle may be about 21 gauge and a distal portion of the needle may be about 19 gauge, or vice versa. The one or more needles may comprise two or more needle portions that are joined together fixedly, permanently, temporarily, or a combination thereof. The two or more needle portions may be the same gauge, or may be different gauges. One or both of the needle portions may include an interior size or region that is generally the same size as the one or more stylets, fiducials, or both. That is, the one or more stylets, fiducials, or both may substantially occupy some, most, or all of the interior of the one or more needles, needle portions, or both. One or both of the needle portions, the needle, or both may be slightly larger than the one or more stylets, fiducials, or both so that the stylets, the fiducials, or both only occupy some of the interior space or region of the one or more needles, needle portions, or both. The one or more needles may include an elongated section, member, or shaft and a distal tip or needle tip. The elongated section, the needle tip, or both may include one or more, or even two or more echogenic markings or scribes. The one or more echogenic features may function to enhance the visibility of the catheter, the needle, the needle tip, or a combination thereof. The one or more echogenic features may function to create one or more echogenic reflections during ultrasonic imaging so that a position or location of the catheter, the needle, and/or the needle tip within the anatomy can be determined. The one or more echogenic features may be or may include one or more scribes, bands, slots, segments, shapes, surfaces, recesses, roughened surfaces, embedded material(s), coatings, grooves, serrations, notches, or a combination thereof. The one or more echogenic features may be one or more dimples, scallops, spiral scribes, helixes, squiggles, angled squiggles, jig-saws, symmetrical shapes, asymmetrical shapes, patterns, dots, dashes, lines, formations, or a combination thereof. The one or more needles may include a distal tip.

The distal end of the needle, the distal tip, the needle tip, or a combination thereof may be configured to function as a piercing tip or feature so that cells, tissue, foreign matter, or a combination thereof can be obtained. The needle tip may be angled, sharply angled, beveled, flat, or a combination thereof so that tissue samples can be cut, cored, scraped from a site or region of interest. The needle tip may include a notched portion, a recessed portion, and/or a lancet tip or feature. A local vacuum may be created or formed at a distal end of the needle, a distal portion, or a needle tip so that tissue samples, foreign matter, or both can be aspirated or moved into the needle, the sample storage area, or both. The one or more needle tips may be contained within the one or more catheters as the catheter is advanced through the anatomy towards the site or region of interest. The one or more needle tips may be advanced or extended past a distal end of the one or more catheters when the catheter is near the region of interest. The one or more needle tips may be generally rigid, flexible, or both. The distal end, the needle tip, or both may include one or more echogenic features. The one or more needles may include one or more sample storage areas.

The one or more stylets may function to steer or guide the one or more needles, catheters, devices, or a combination thereof around the anatomy to the region of interest. The one or more stylets may be disposed within the needle such that the distal ends of the stylet and the needle are substantially aligned. The one or more stylets may function to block or prevent debris (i.e., tissue, blood, and the like) from entering the needle as needle is advanced towards a site or region of interest. The one or more stylets may be formed from a single material, or may be formed from one or more materials. The one or more stylets may be fabricated from any suitable material. The one or more stylets may be made from a metal or metal alloy, such as stainless steel, nitinol, or the like. The one or more stylets may be formed from a shape memory material (i.e., metal or polymer). The one or more stylets may comprise a polymer or other suitable covering over at least a portion of the length of the stylets. The one or more stylets may be at least partially rigid, at least partially flexible, or both. The one or more stylets may include one or more portions (i.e., a distal portion, a proximal portion, or a portion in between) that are at least partially rigid, at least partially flexible, or both. The one or more stylets may be at least partially flexible, bendable, articulable, or a combination thereof so that the stylet can be positioned along a central lumen, opening, and/or interior portion of the needles. The one or more stylets may bend or articulate about 15 degrees or more, about 45 degrees or more, about 60 degrees or more, about 90 degrees or more, about 110 degrees or more, or even about 130 degrees or more. The one or more stylets may have a generally uniform cross section, or the cross section may be variable. At least a portion of the outer surface of the one or more stylets may be substantially the same size as the interior of one or more needle portions of the one or more needles so that the stylet substantially occupies some, most, or all of the interior of the needle. The one or more stylets may be advanced, actuated, or moved from a retracted position to an advanced position. In the retracted position, the distal end of the one or more stylets may be offset or retracted from the distal end of the one or more needles for receiving one or more fiducials between the distal end of the stylet and the distal end of the needle. In the advanced position, the distal end of the one or more stylets may be substantially aligned with the distal end of the one or more needles to form a substantially continuous surface or edge. When the needle and stylet extend beyond a distal end of the catheter, the needle can penetrate and separate tissue without coring, ripping, or damaging the tissue. The one or more stylets may include one or more notched portions, recesses, cut-outs, or grooves. The one or more notched portions, recesses, cut-outs, or grooves may be located at a distal end, or at a location between the distal and proximal ends of the stylet. The one or more stylets may be at least partially withdrawn from the one or more needles to allow insertion of one or more fiducials at the proximal end of the needle.

The one or more fiducials may function to provide an improved visual target for a target tissue in a region of interest. The one or more fiducials may be delivered by a stylet or separated from a stylet. The one or more fiducials may be formed from a single material, or may be formed from one or more materials. The one or more fiducials may be fabricated from any suitable material. The one or more fiducials may be made from a metal or metal alloy, such as stainless steel, nitinol, or the like. The one or more fiducials may be formed from a shape memory material (i.e., metal or polymer). The one or more fiducials may comprise a polymer or other suitable covering over at least a portion of the length of the fiducials. The one or more fiducials may be at least partially rigid, at least partially flexible, or both. The one or more fiducials may include one or more portions (i.e., a distal portion, a proximal portion, or a portion in between) that are at least partially rigid, at least partially flexible, or both. The one or more fiducials may be at least partially flexible, bendable, articulable, or a combination thereof so that the fiducial can be positioned along a central lumen, opening, and/or interior portion of the needles. The one or more fiducials may bend or articulate about 15 degrees or more, about 45 degrees or more, about 60 degrees or more, about 90 degrees or more, about 110 degrees or more, or about 130 degrees or may bend into a coil of various diameters and numbers of loops. The one or more fiducials may have a generally uniform cross section, or the cross section may be variable. At least a portion of the outer surface of the one or more fiducials may be substantially the same size as the interior of one or more needle portions of the one or more needles so that the fiducial substantially occupies some, most, or all of the interior of the needle. The one or more fiducials may be advanced, actuated, or moved from a retracted position to an advanced position. In the retracted position, the distal end of the one or more fiducials may be offset or retracted from the distal end of the one or more needles. In the advanced position, the distal end of the one or more fiducials may be substantially aligned with the distal end of the one or more needles to form a substantially continuous surface or edge. When the needle and fiducial extend beyond a distal end of the catheter, the needle can penetrate and separate tissue without coring, ripping, or damaging the tissue. The one or more fiducials may include one or more notched portions, recesses, cut-outs, or grooves. The one or more notched portions, recesses, cut-outs, or grooves may be located at a distal end, or at a location between the distal and proximal ends of the fiducial.

One or more cartridges may be attached to the bronchoscope, the needle handle or a combination thereof. The one or more cartridges may function to deliver a fiducial(s) to the distal end of the catheter and/or the needle. The one or more cartridges and the included fiducial(s) may be received in a sterilized package. The one or more cartridges may include a plunger for delivering the fiducial into the bronchoscope and/or the needle handle. The one or more cartridges may include an inner lumen with a size for receiving the fiducial and/or the plunger. The one or more cartridges or the plunger may be formed of a see through material (e.g., glass, plastic tubing) or may be an opaque material.

Figure 1:
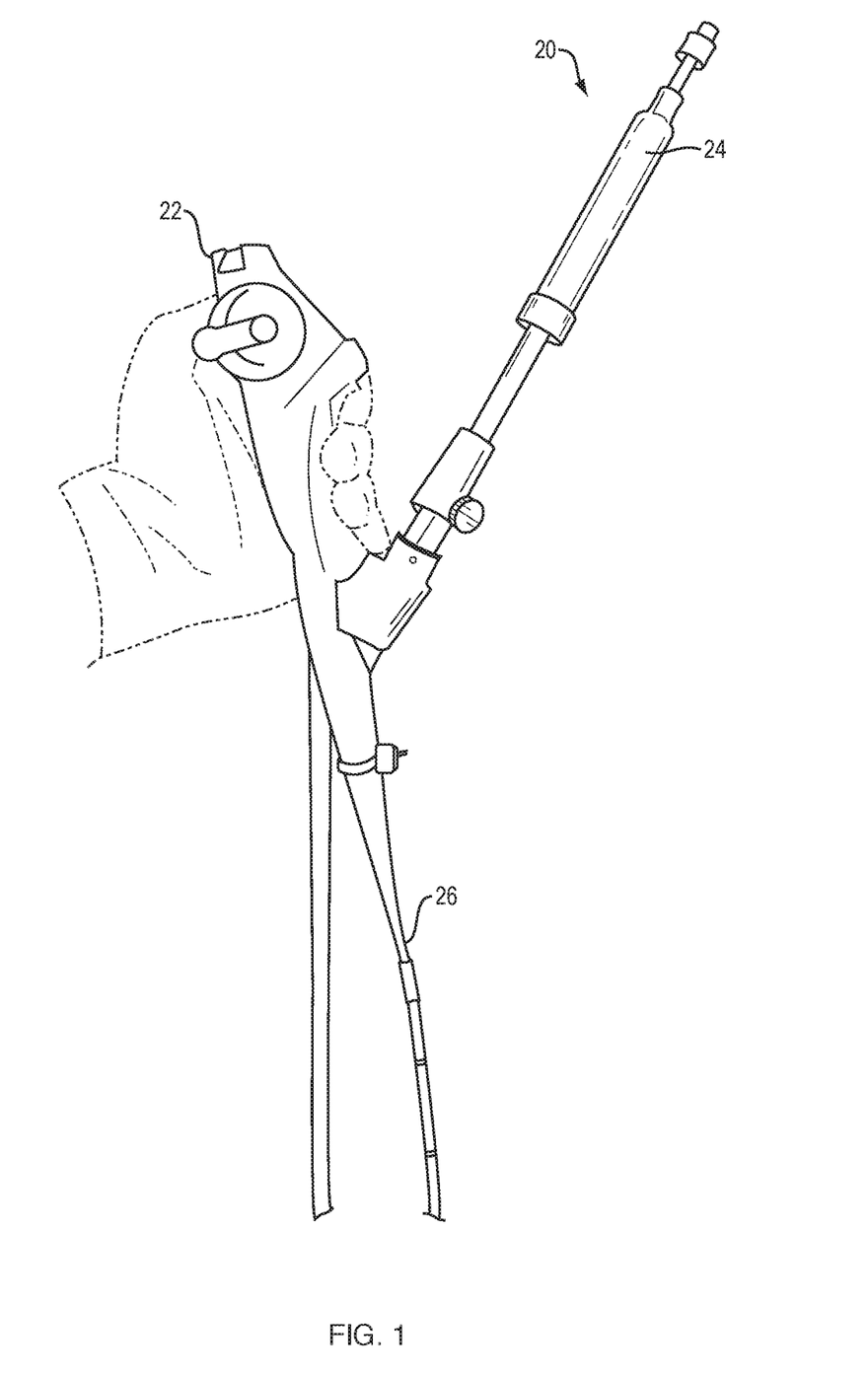
FIG. 1 illustrates a perspective view of a device including a bronchoscope having a needle handle according to the teachings herein.
Figure 2:
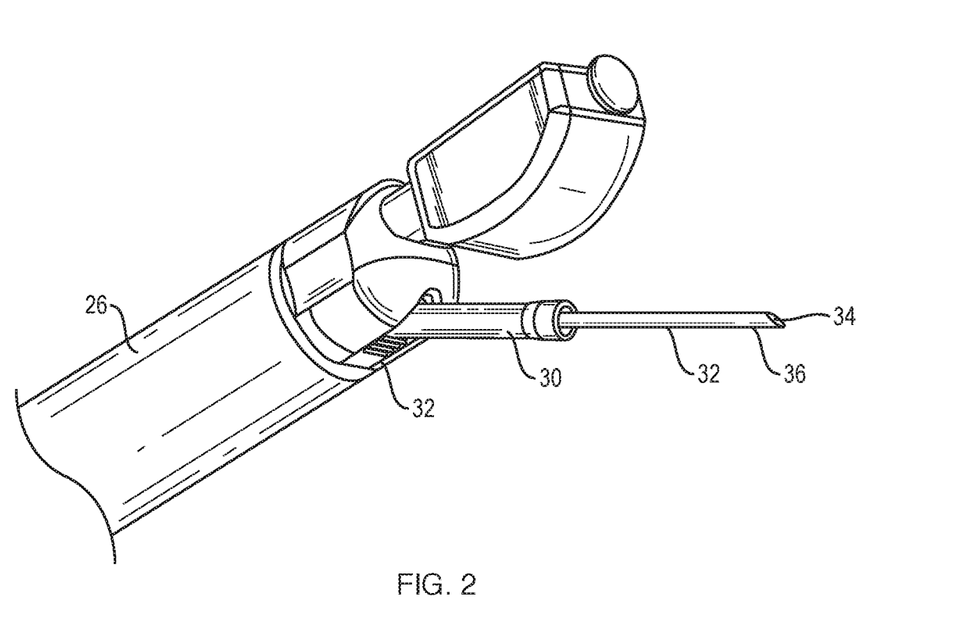
FIG. 2 illustrates a partial perspective view of a distal end of a catheter with protruding needle according to the teachings herein.

FIG. 1 illustrates a system 20 including a bronchoscope 22 with a detachable needle handle 24 and a catheter 26. FIG. 2 illustrates a sheath 30 that extends from a working channel 32 of the catheter 26 of the bronchoscope 22, and includes therein a needle 32 with a needle tip 34 at a distal end 36 of the needle 32.

Figure 3:
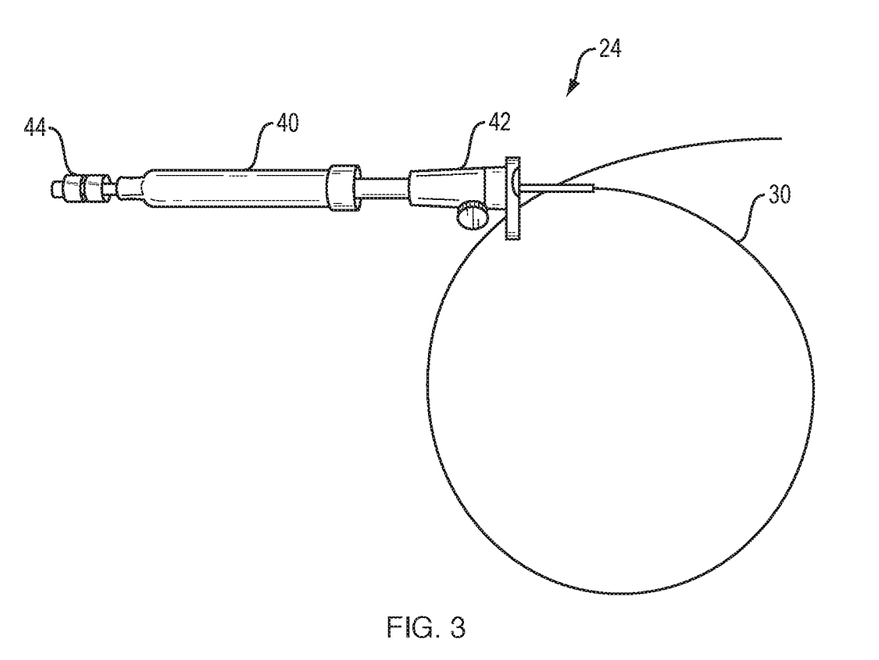
FIG. 3 illustrates a perspective view of a needle handle device according to the teachings herein.

FIG. 3 illustrates aspects of the needle handle 24. The needle handle 24 may include a first section 40 connected to the needle 32 (not shown) and a second section 42 connected to the sheath 30. The needle handle 24 may include a stylet (not shown) located within the needle 32 (not shown). The stylet may connect to a stylet handle 44. The stylet may be removably received within the needle handle 24 at a proximal end of the first section 40. The stylet is disposed in the interior of the needle 32 (not shown).

Figure 4A:
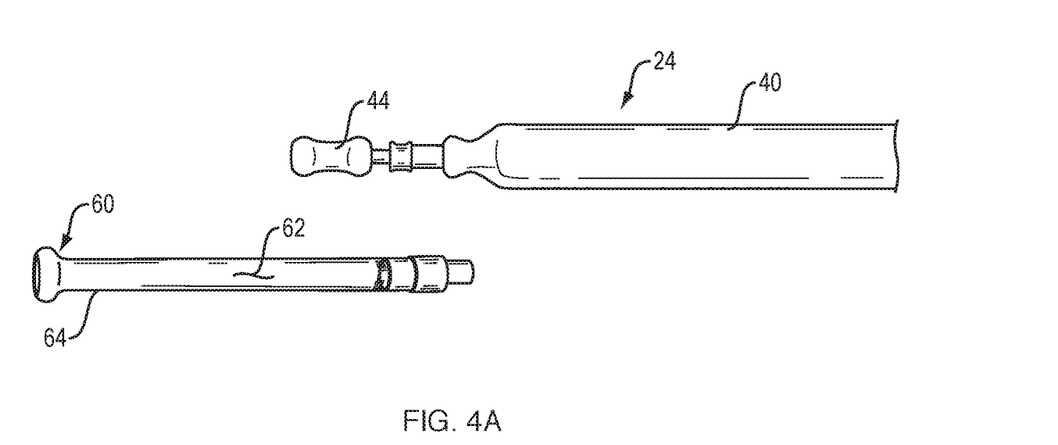
FIGS. 4A-4C illustrate perspective views of a fiducial delivery device during a process of loading a fiducial into a needle handle according to the teachings herein.
Figure 4B:
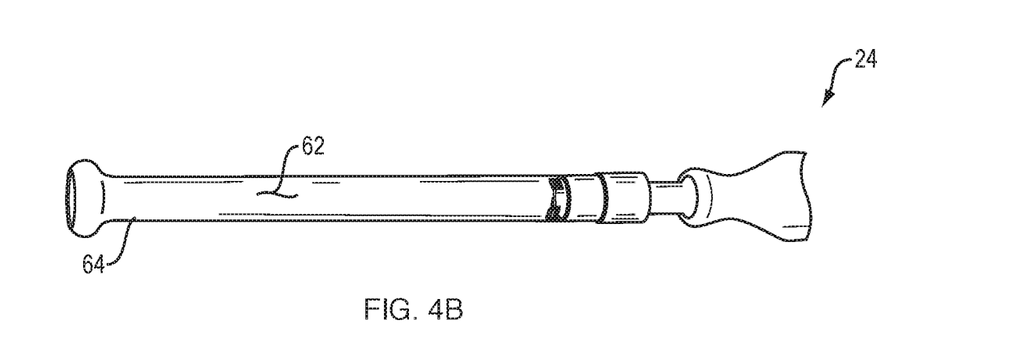
Figure 4C:
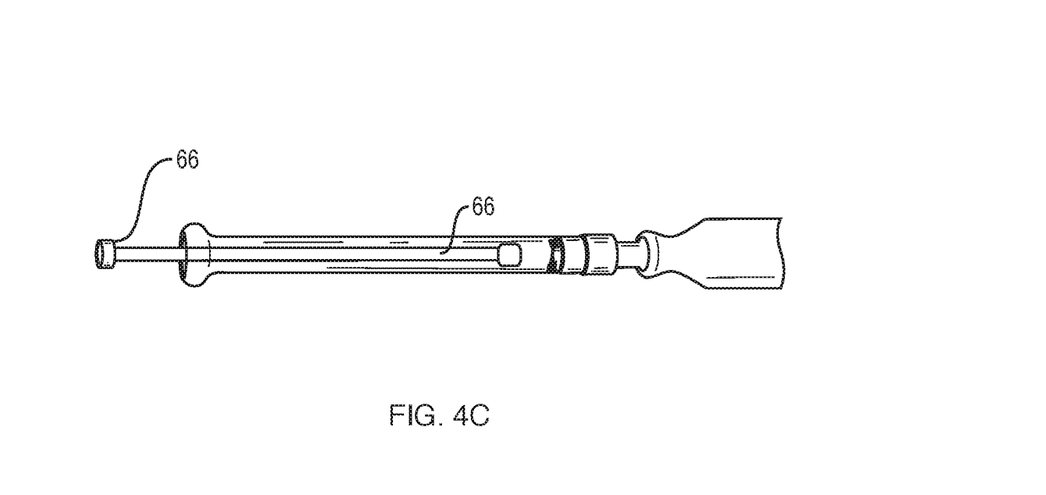

FIGS. 4A-4C illustrate a portion of a fiducial delivery device 60 that may include a pre-loaded fiducial coil 62. The fiducial coil 62 may be made of a shape memory material that is shape set to a coil or other configuration. Before the fiducial coil 62 is loaded into a cartridge 64, it is placed in an uncoiled state. The cartridge 64 may attach to the proximal end of the needle handle 24 after removal of the stylet. The device 60 may include a plunger 66 that is received within the housing. The plunger 66, when fully inserted into the cartridge 64, pushes the fiducial coil 62 into the first section 40 of the needle handle 24. The fiducial coil 62 is delivered to the distal end 36 of the needle 32 by the stylet after the device 60 has been removed from the needle housing 24 and the stylet has been reinserted. When the distal end 36 of the needle 32 is positioned at a tissue that an operator desires to attach the fiducial coil 62 to, the stylet is advanced forcing the fiducial coil 62 to exit the needle 32 into or near the target tissue. As the fiducial coil 62 is heated, the fiducial coil 62 returns to its shape set configuration, e.g. a coil.

Figure 5A:
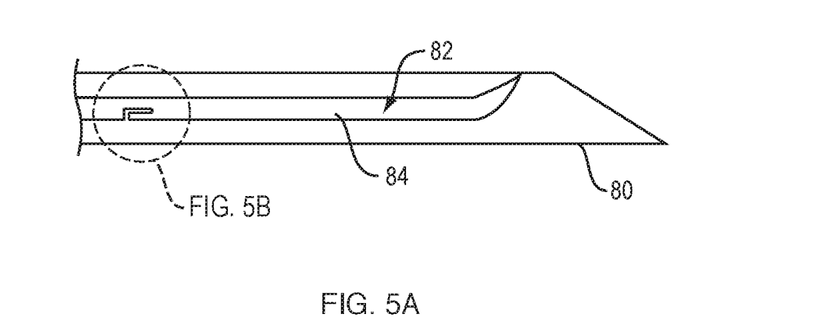
FIGS. 5A-5F illustrate side x-ray views of a detachable fiducial device and needle according to the teachings herein.

FIG. 5A illustrates a distal end of a needle 80 that includes a stylet 82. The stylet 82 may include a fiducial coil detachable portion 84 that may be formed of a shape memory alloy, such as stainless steel, nitinol, or the like. The fiducial coil detachable portion 84 is shape set in a desired shape, such as a coil, helical or other shape. When the fiducial coil detachable portion 84 is inserted into the needle 80 it is deformed from its original shape to one that will allow it to fit within the needle 80. Once the fiducial coil detachable portion 84 exits the needle 80, the heat from the surrounding tissue causes the fiducial coil detachable portion 84 to return to its shape set state (a coil in this example) —see FIG. 5C.

Figure 5B:
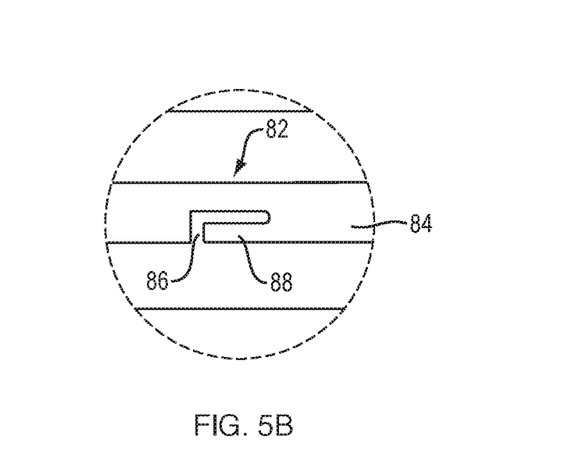
Figure 5C:
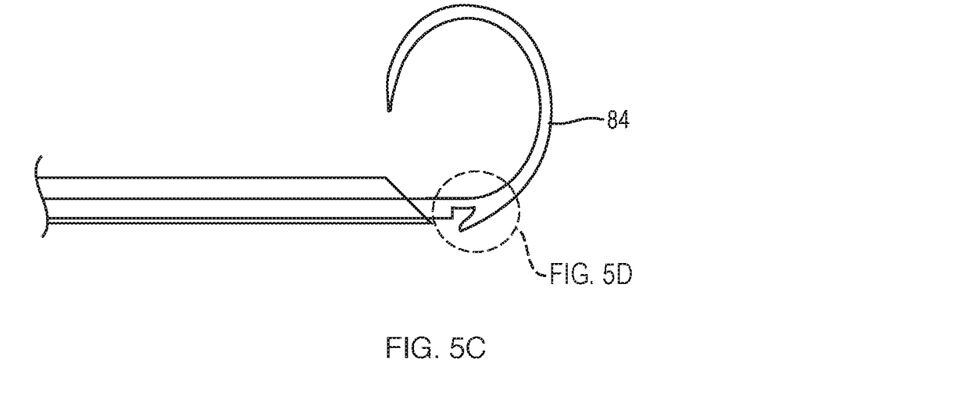
Figure 5D:
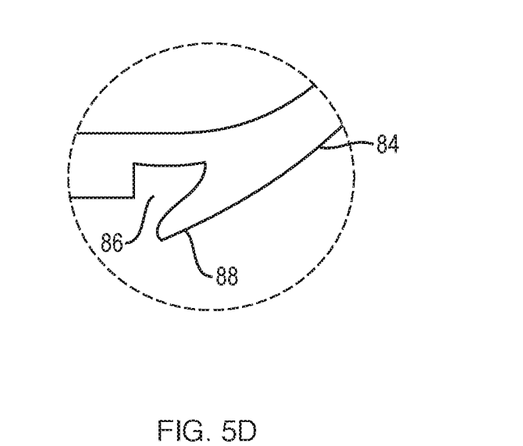
Figure 5E:
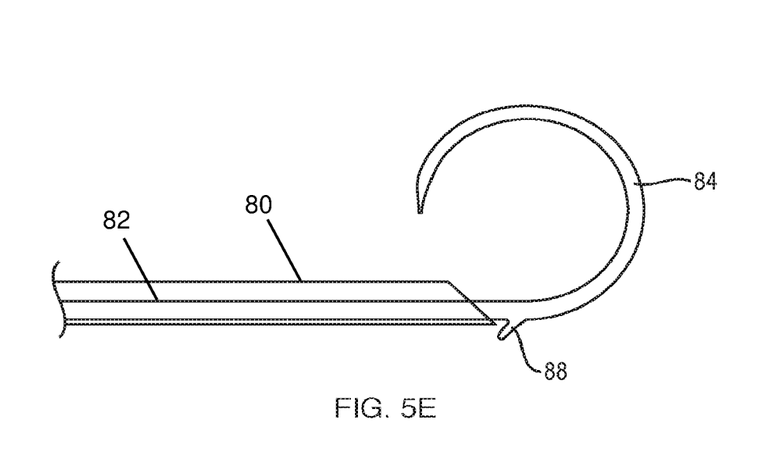
Figure 5F:
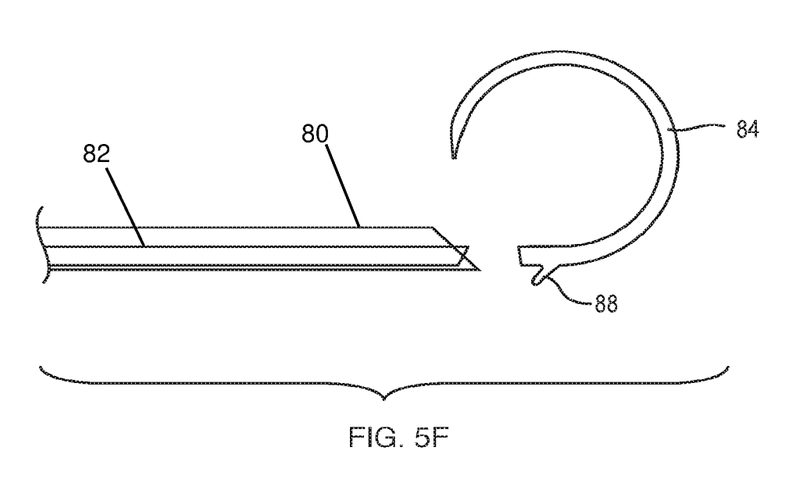

FIG. 5B illustrates a transition location between the fiducial coil detachable portion 84 and the remainder of the stylet 82. The transition location may include a notch 86 that has been etch and/or machined into the material at the transition location. The notch 86 may be located at an edge that coincides with an outer edge when the fiducial coil detachable portion 84 is in its memory shape state. The notch 86 creates a tab 88. As shown in FIGS. 5C and 5D, the tab 88 deflects away from a centerline of the fiducial coil detachable portion 84, thus protruding away from an outer edge of the proximal end of the stylet. As shown in FIGS. 5E and 5F, the stylet 82 is retracted into the needle 80, thus causing the tab 88 to catch on the edge of the needle 80. The pressure on the tab 88 by the needle edge causes a fracture to occur at or near the notch 86 at the transition location, thus leading to eventual separation/deployment of the fiducial coil detachable portion 84.

Figure 6A:
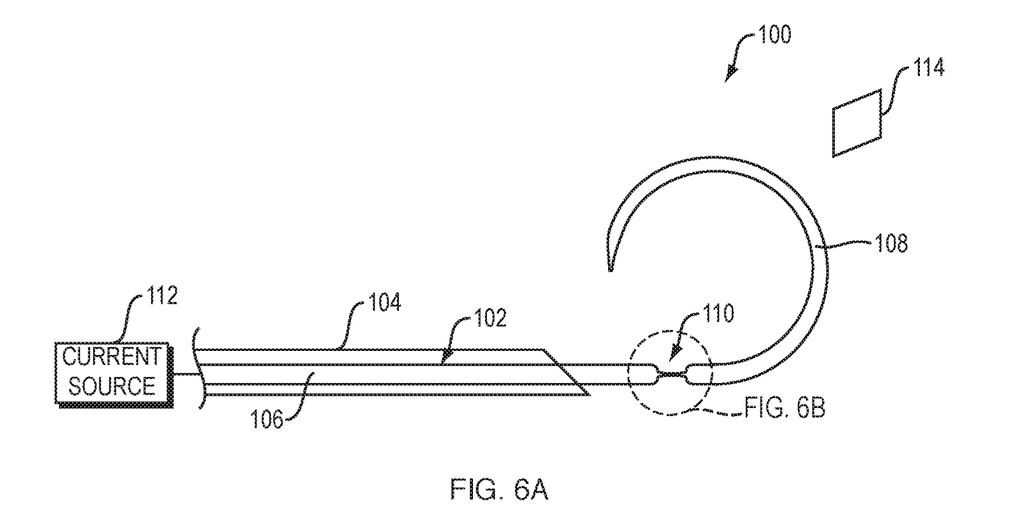
FIGS. 6A-6C illustrate side x-ray views of another detachable fiducial device and needle according to the teachings herein.
Figure 6B:
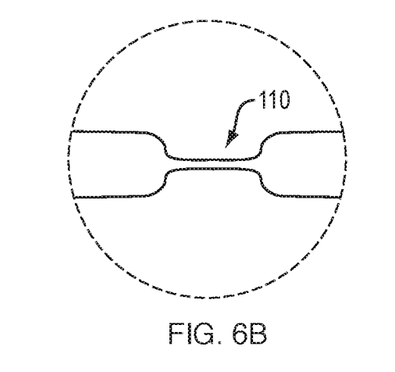
Figure 6C:
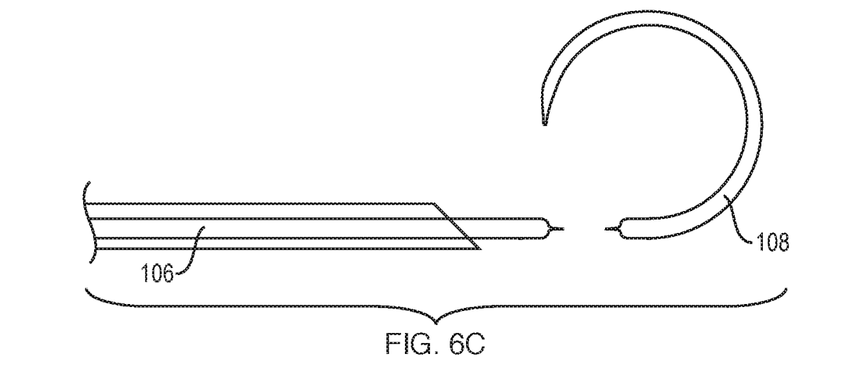

FIGS. 6A-6C illustrate a fiducial coil device 100 that uses an electric current or charge to effect fiducial separation. The device 100 may include a stylet 102 received within a needle 104 and a grounding pad 114. The stylet 102 may include a base section 106, a coil section 108 and a separation section 110. The coil section 108 may be formed of a shape memory alloy, such as stainless steel, nitinol, or the like. The coil section 108 is created in a desired shape, such as a coil, helical or other shape. When the coil section 108 is inserted into the needle 104 it is deformed from its original shape to one that will allow it to fit within the needle 104. Once the coil section 108 exits the needle 104 the heat from the surrounding tissue causes the coil section 108 to return to its shape set configuration (a coil in this example) —see FIG. 6A. After the coil section 108 is at its memory shape, an operator activates the current source 112 to supply a current stylet. The grounding pad 114 acts to complete a circuit including the current source 112 and the stylet. This applied current causes the separator section 110 heat up and fail much like a circuit fuse. The applied current may be between 1 and 10 mA. Other current values may be used even those produced when the current source 112 is in a high power or a coagulation mode of operation, thus producing currents greater than 0.1 A, for example 0.6 A. Other current values may depend upon the material selected for the separation section 110, the power level of the current source 112 or other factors. The Olympus ESG-100 generator IFU is an example of the current source 112.

Figure 7A:
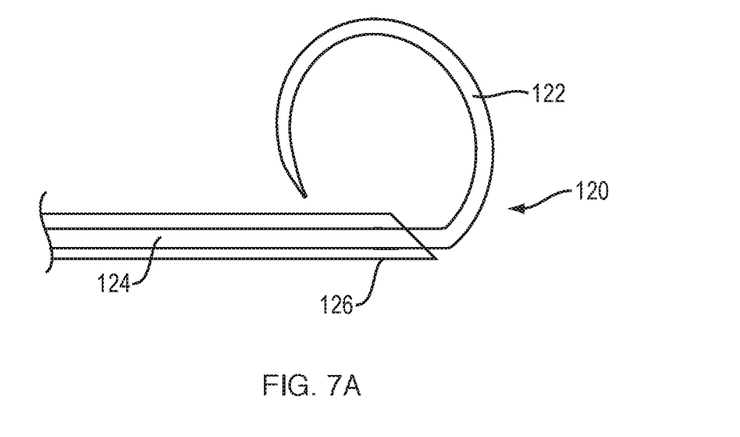
FIGS. 7A-7B illustrate side x-ray views of still another detachable fiducial device and needle according to the teachings herein.
Figure 7B:
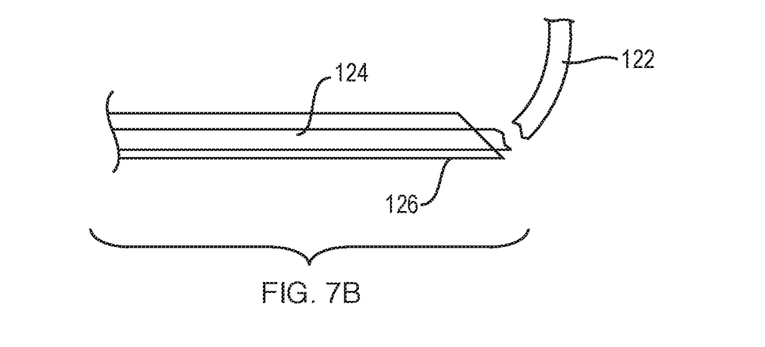

In another teaching as shown in FIG. 7A, a stylet 120 is shape-set to cause a sharp bend at a location between a coil section 122 and a base section 124. When the coil section 122 exits a needle 126, a sharp rise in stress occurs at the location between the coil section 122 and the base section 124 due to the sharp bend. As the operator retracts the stylet 120 into the needle 126, the applied pressure by needle 126 on the coil section 122 causes fracture at the location between the coil section 122 and the base section 124—see FIG. 7B.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

The omission in the following claims of any aspect of subject matter that is disclosed herein is not a disclaimer of such subject matter, nor should it be regarded that the inventors did not consider such subject matter to be part of the disclosed inventive subject matter.

LIST OF REFERENCE NUMERALS 20 system
22 bronchoscope
24 needle handle
26 catheter
30 sheath
32 needle
34 needle tip
36 distal end
40 first section
42 second section
44 stylet handle
60 fiducial delivery device
62 fiducial coil
64 cartridge
66 plunger
80 needle
82 stylet
84 fiducial coil detachable portion
86 notch
88 tab
100 fiducial coil device
102 stylet
104 needle
106 base section
108 coil section
110 separation section
112 current source
114 grounding pad
120 stylet
122 coil section
124 base section
126 needle

The invention claimed is:

1. A device comprising:
  a handle device;
  a catheter comprising a proximal end and a distal end, wherein the proximal end of the catheter is coupled to the handle device;
  a needle slidably received within the catheter, the needle comprising a proximal end and a distal end; and
  a monolithic material slidably received within the needle, the monolithic material comprising:
    a stylet comprising a proximal end and a distal end;
    a fiducial marker comprising a proximal end and a distal end, wherein the fiducial marker is configured to transition from having a first shape state inside the needle to having a second shape state upon expulsion from the distal end of the needle; and
    a failure section that mechanically couples the distal end of the stylet to the proximal end of the fiducial marker, the failure section configured to: (i) apply a force to expel the fiducial marker from the distal end of the needle in response to distal movement of the stylet, and (ii) mechanically separate the stylet from the fiducial marker in response to proximal movement of the stylet.

2. The device of claim 1, further comprising: a cartridge device comprising:
  a housing having a proximal end and a distal end, the distal end of the housing configured to attach to the handle device, the housing configured to receive the fiducial marker when in the first shape state; and
  a plunger configured to move the fiducial marker to the distal end of the housing and into the handle device.

3. The device of claim 1, wherein the failure section comprises a notch, wherein separation of the stylet from the fiducial marker occurs after application of a force to the notch during the fiducial marker delivery state.

4. The device of claim 3, wherein the second shape state comprises a shape set coil shape, wherein the notch is adjacent to an external circumference edge of the shapeset coil shape.

5. The device of claim 1, further comprising: a grounding pad; and
a current source electrically coupled to the stylet and fiducial marker,
wherein separation of the stylet from the fiducial marker occurs after failure of the failure section due to application of a current above a threshold value by the current source to the stylet and fiducial marker during the fiducial marker delivery state.

6. The device of claim 1, wherein the failure section comprises a cross section having a smaller area than cross sections of the distal end of the stylet and the proximal end of the fiducial marker.

7. The device of claim 1, wherein the second shape state comprises a shape set coil shape, wherein separation of the stylet from the fiducial marker occurs after application of a force to the fiducial marker during the fiducial marker delivery state.

8. A device comprising:
a needle comprising a proximal end and a distal end; and
a monolithic fiducial marker device received within the needle, the fiducial marker device comprising:
  a proximal end;
  a distal end, the distal end of the fiducial marker device having a first shape state and a second shape state, the distal end of the fiducial marker device is in the first shape state inside the needle, the distal end of the fiducial marker device transitions from the first shape state to the second shape state upon expulsion from the distal end of the needle; and
a failure section that mechanically couples the proximal end and the distal end of the fiducial marker device, the failure section includes a tab configured to deflect away from a centerline of the stylet upon exiting the distal end of the needle,
wherein separation of the proximal and distal ends of the fiducial marker device at the failure section occur after application of at least one of a force or an electric current at or near the failure section, the separation producing a fiducial marker.

9. The device of claim 1, wherein the failure section includes a tab configured to deflect away from a centerline of the stylet upon exiting the distal end of the needle.

10. The device of claim 9, wherein the tab is configured to make contact with the distal end of the needle upon proximal motion of the stylet relative to the needle, thus imparting a force on the tab configured to cause failure of the failure section.

11. The device of claim 8, wherein the tab is configured to make contact with the distal end of the needle upon proximal motion of the stylet relative to the needle, thus imparting a force on the tab configured to cause failure of the failure section.

* * * * *